United States Patent

Hartmann et al.

[11] Patent Number: 6,082,622
[45] Date of Patent: *Jul. 4, 2000

[54] METHOD AND SYSTEM FOR STORING AND PREPARING DATA USING A DATA MEMORY CARD

[75] Inventors: Georg Hartmann, Köln; Gunnar Weikert, Düsseldorf, both of Germany

[73] Assignee: Bayer Aktiengesellschaft, Leverkusen, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/757,410

[22] Filed: Nov. 27, 1996

Related U.S. Application Data

[63] Continuation-in-part of application No. 08/451,819, May 26, 1995, abandoned.

[30] Foreign Application Priority Data

Jun. 3, 1994 [DE] Germany ............... 44 19 576

[51] Int. Cl.[7] .................................. G06K 19/00
[52] U.S. Cl. .................. 235/492; 235/380; 235/382
[58] Field of Search ................. 235/492, 487, 235/375, 380, 382

[56] References Cited

U.S. PATENT DOCUMENTS

| | | | |
|---|---|---|---|
| 4,159,417 | 6/1979 | Rubincam | 235/375 |
| 4,837,422 | 6/1989 | Dethloff et al. | 235/380 |
| 4,904,853 | 2/1990 | Yokokawa | 235/487 |
| 4,958,837 | 9/1990 | Russell | 273/237 |
| 5,111,539 | 5/1992 | Hiruta et al. | 4/661 |
| 5,161,826 | 11/1992 | Van Giesen et al. | 283/77 |
| 5,185,798 | 2/1993 | Hamada et al. | 235/382 |
| 5,317,138 | 5/1994 | Togawa | 235/440 |
| 5,411,259 | 5/1995 | Pearson et al. | 273/93 |
| 5,517,014 | 5/1996 | Iijima | 902/26 |
| 5,521,362 | 5/1996 | Powers | 235/380 |
| 5,544,246 | 8/1996 | Mandelbaum et al. | 235/379 |
| 5,578,808 | 11/1996 | Taylor | 235/379 |
| 5,597,182 | 1/1997 | Reber et al. | 283/67 |
| 5,815,252 | 9/1998 | Price-Francis | 235/492 |

FOREIGN PATENT DOCUMENTS

0528275 A2  8/1992  European Pat. Off. .

OTHER PUBLICATIONS

IBM Technical Disclosure Bulletin, vol. 19, No. 12, May 1977, USA, 4800–4801.

*Primary Examiner*—Donald Hajec
*Assistant Examiner*—Drew A. Dunn
*Attorney, Agent, or Firm*—Norris, McLaughlin & Marcus, P.A.

[57] ABSTRACT

A system and method of storing and preparing data uses at least one data memory card having at least one electronic memory chip and a separate optical memory. At frequent intervals alphanumeric data is entered into the at least one electronic memory chip. At less frequent intervals, image data is entered into the optical memory, data is read from the at least one electronic memory chip and data is transferred from the at least one electronic memory chip into the optical memory.

4 Claims, 1 Drawing Sheet

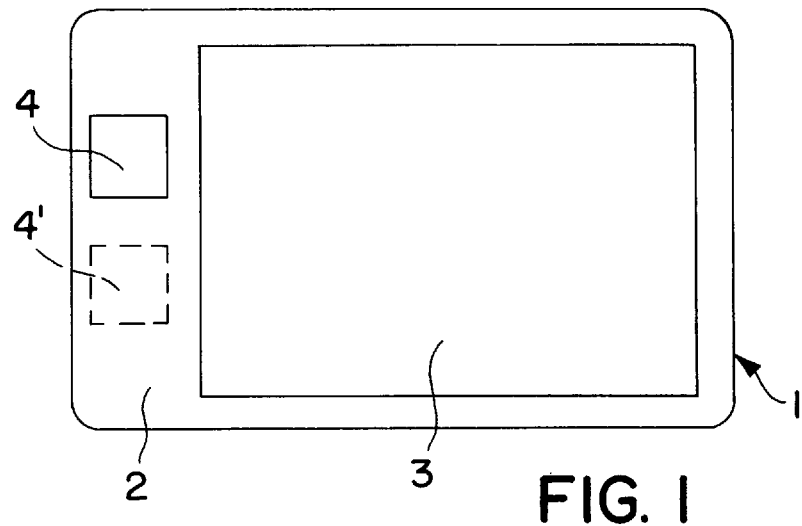
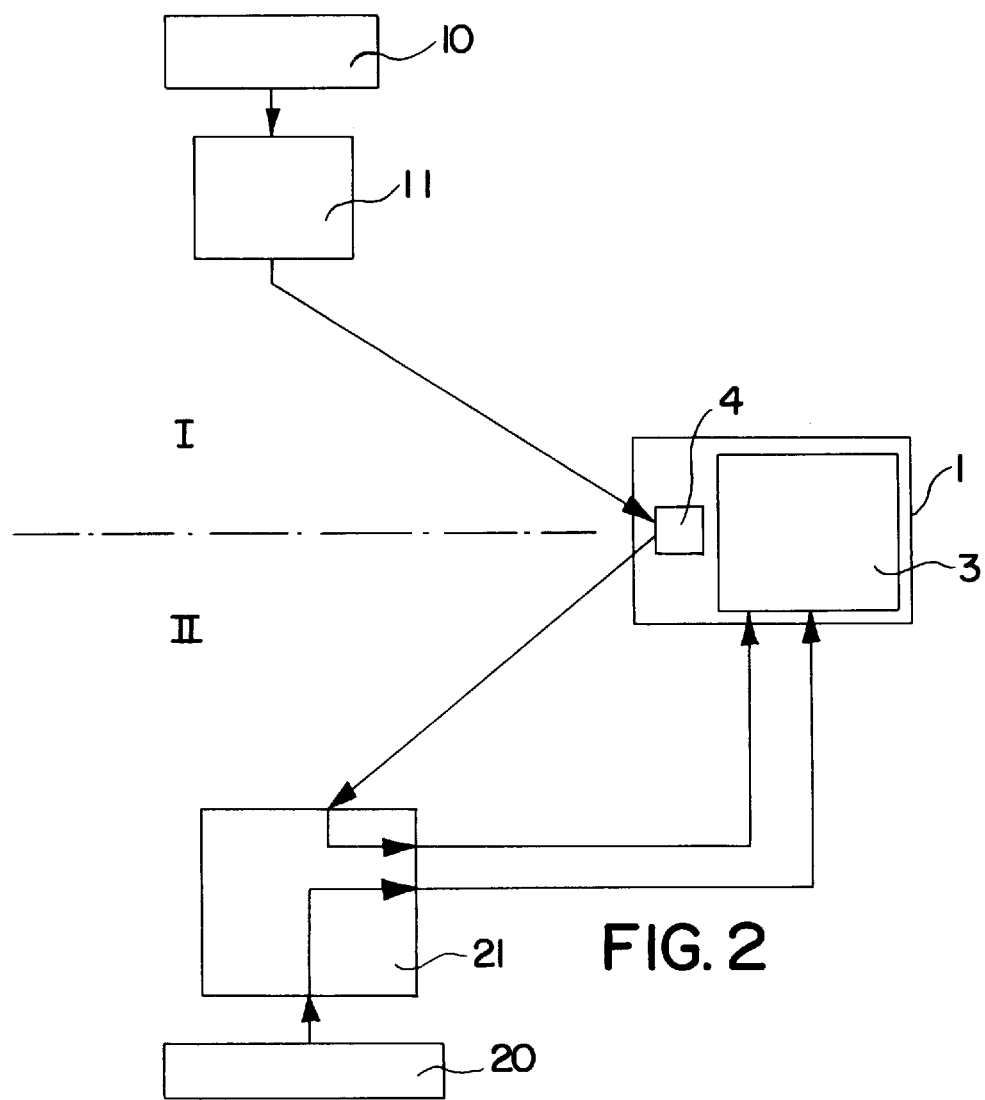

METHOD AND SYSTEM FOR STORING AND PREPARING DATA USING A DATA MEMORY CARD

This is a continuation-in-part of application Ser. No. 08/451,819 filed May 26, 1995, now abandoned.

BACKGROUND OF THE INVENTION

The present invention relates to a method of storing and preparing on the one hand alphanumeric data occurring at short periodic intervals and on the other hand image material occurring at long periodic intervals, using a personal card as the storage medium.

In the long-term observation of sequences, there often occur on the one hand data which are picked up at short periodic intervals, for example several times a day, and on the other hand image material generated at greater time intervals for assessing long-term changes, a relationship existing, or having to be deduced, between the alphanumeric data determined at short periodic intervals and the long-term changes.

Such long-term observations may concern, for example, patients with chronic disorders. In such cases there may occur on the one hand data which the patient himself determines without involvement of the doctor at short time intervals in the form of alphanumeric data and which are to be available for the medical examinations carried out at greater time intervals, since they provide important indications for the further therapy of long-term changes possibly discovered by the doctor. The long-term observation by the doctor on the basis of examinations at relatively great time intervals, for example including photographic comparative examinations, can be supplemented by the preparation of the short-term observations determined by the patient himself and can contribute to increase effectiveness of the therapy.

The long-term observation of a diabetic by a doctor comprises, for example, inter alia, half-yearly comparative examinations of the ocular fundus, in each case photographic records of the ocular fundus being produced and compared. On the other hand, the patient determines, inter alia, his blood-sugar level several times a day. The evaluation of short-term variations in the blood-sugar level can provide the doctor with important indications in conjunction with changes of the ocular fundus.

For effective long-term therapy, it is consequently desirable to have available in each case both the observations carried out by the patient at short periodic intervals and the comparative examinations carried out at longer periodic intervals. In the interests of the mobility of the patients, it would be desirable furthermore for the patient to be able to carry on him the data required for a highly informative case history.

Therefore, it has already been proposed on several occasions (see e.g. European-Patent Application 467,693) to use as the storage medium for health-relevant data optical memory cards in credit card format which can be written to and read from by means of laser-beams ("WORM"=Write Once Read Many Memory). On account of technical development in recent years, such optical memory cards have achieved storage capacities of several megabytes, in particular 4 to 6 megabytes. The corresponding reading/writing devices for such optical memory cards are not suitable, however, to be carried on a patient.

SUMMARY OF THE INVENTION

Therefore, it is proposed according to the invention to use data memories in credit card format which have a first memory for optical data storage and a second memory in the form of an electronic chip (so called hybrid cards, see e.g. U.S. Pat. No. 5,185,798 to Hamada et al.) For writing to the electronic chip, only devices having the dimensions of a pocket calculator are available, e.g. from SAFEWARE AG, D-8919 Greifenberg, Germany, under the tradename SAFE-CARDREADER, which can be readily carried on a patient. The writing device for the chip can be combined, furthermore, with a device for determining the blood sugar, so that the daily blood-sugar measurement of the patient is written directly into the chip of the memory card. As part of the, for example, half-yearly examinations by the doctor, the latter will call up the stored blood-sugar values, initially process them if necessary, so that they can be read in the form of a diagram with a time axis, and transfer them together with the ocular fundus image into the optical memory area. The chip memory is then available once again for the recording of blood-sugar values.

A read/write/data processing-unit for hybrid cards having access to both the chip memory and the optical memory is also disclosed in the Hamada et al. patent.

The subject of the present invention now is a method of storing and preparing alphanumeric data occurring at short periodic intervals and image material occurring at long periodic intervals which is characterized in that the alphanumeric data are stored at short periodic intervals by an alphanumeric writing device on a first memory in the form of an electronic memory chip of a data carrier card, the image material are stored by means of an optical reading/writing device in a memory in the form of an optical memory area of the same data carrier card, the storage of image material being accompanied at a related time in each case by the chip being read, processed if necessary and the possibly processed data being transferred to the optical memory area.

The subject of the present invention is also the unit comprising a data memory card, containing at least at first optical data memory and a second electronic chip memory, a writing device for writing to the chip only and also a reading/writing device having access to both the chips and the optical data memory.

The method according to the invention and the unit according to the invention are suitable everywhere where it is required to rather alphanumeric data, preferably in a mobile manner, which are evaluated in conjunction with photographic comparative records prepared at greater time intervals. Such data structures occur not only in the case of chronic disorders, but also in conjunction with workplaces where there are hazardous conditions, if for example MAC values are measured and stored within short periodic intervals and more extensive healthcare or monitoring examinations are carried out at greater time intervals, including for example X-ray records.

Furthermore, the method according to the invention and the unit according to the invention may be advantageous in conjunction with the trial use of drugs, both in animal testing and in human testing. It may also be expedient, however, in the observation of building structures or vehicles, generally in conjunction with the monitoring of material fatigue, to assign to the object under observation in each case a "personal" card, where on the one hand alphanumeric data, for example vibration behaviour, loading values and the like are registered at short intervals and, for example, X-ray records of welds are produced in the form of image information material at greater intervals.

The chip of the data memory card may in this case contain additional information for identifying the object under observation or the patient. On the other hand, it is also possible to provide the data memory card with a plurality of chips, one of the chips being intended for the storage of such identification data. A further possibility is for the data memory card to be provided with an additional magnetic strip for recording the data for identifying the object under observation or the patient.

The method according to the invention and the unit according to the invention are of advantage in particular whenever alphanumeric data are to be generated and stored at short periodic intervals in an unlocalized manner and independently of an energy supply and are then to be made available at longer periodic intervals, if necessary after evaluation, for example by means of electronic data processing systems, in conjunction with the generation of comparative image material for further later evaluations. In this case, on the one hand the limited storage capacity of the chip, which is about 5 KB, is used in combination with the high storage capacity of an optical memory card. According to the invention, this requires the compatibility of the data memory card on the one hand with a mobile, low-volume and lightweight, battery-operated writing device for the chip storage and on the other hand with a substantially stationary chip-reading, data-processing and reading/writing device for optical data memories.

BRIEF DESCRIPTION OF THE DRAWINGS

FIG. 1 is a top view of a data memory card used according to the present invention.

FIG. 2 is a block diagram of the system for carrying out the method of the present invention.

DETAILED DESCRIPTION OF THE INVENTION

The data memory card to be used according to the invention is represented in the attached FIG. 1. The data memory card 1 contains in a frame 2 an optical data memory field 3 and the chip 4, it being possible for a second chip 4' to be provided, if necessary.

FIG. 2 shows the data flow according to the invention. Above the dash-dotted line in the area of short-term periodic data sampling (I) is the portable write unit 11 to write alphanumeric data 10 occurring at short and possibly at differing locations into the chip memory 4 of the card 1. Below the dash-dotted line (area II) is a stationary read/write/processing-unit 21 to write image material data 20 into the optical memory 3 of the card 1 and to read alphanumeric data stored at short term periods in the chip memory 4, process them, and write the processed data into the optical memory 3 of the card 1.

What is claimed is:

1. A method of storing and preparing data comprising the steps of:

providing at least one data memory card having at least one electronic memory chip and a separate digital optical memory;

at frequent intervals entering alphanumeric data into the at least one electronic memory chip; and at less frequent intervals entering digital data representative of an image into the digital optical memory, reading data from the at least one electronic memory chip and transferring data from the at least one electronic memory chip as digital data into the digital optical memory.

2. The method according to claim 1, for storing and preparing data relating to a chronic health disorder, wherein test data relating to the disorder is entered into the at least one electronic memory chip at least once per day and image data and stored test data in the at least one memory chip is entered into the optical memory no more than twice a year.

3. A system for storing and preparing data comprising:

at least one data memory card having at least one electronic memory chip and a separate digital optical memory;

a device for entering alphanumeric data into the at least one electronic memory chip at frequent intervals; and a device for entering digital data representative of an image into the digital optical memory, reading data from the at least one electronic memory chip and transferring data from the at least one electronic memory chip as digital data into the digital optical memory at less frequent intervals.

4. The system according to claim 3, wherein the device for entering alphanumeric data into the at least one electronic memory chip at frequent intervals is compact and portable.

* * * * *